(12) United States Patent  
Francescatti et al.

(10) Patent No.: US 7,678,040 B2  
(45) Date of Patent: Mar. 16, 2010

(54) CUSTOMIZED GYNECOLOGICAL BRACHYTHERAPY APPLICATOR AND METHOD

(75) Inventors: Darius Francescatti, Barrington, IL (US); Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 164 days.

(21) Appl. No.: 11/809,836

(22) Filed: May 31, 2007

(65) Prior Publication Data  
US 2008/0300445 A1  Dec. 4, 2008

(51) Int. Cl.  
*A61N 5/00* (2006.01)

(52) U.S. Cl. .......................................................... 600/6

(58) Field of Classification Search ............... 600/1–8; 604/27, 28  
See application file for complete search history.

(56) References Cited

U.S. PATENT DOCUMENTS

| | | | |
|---|---|---|---|
| 3,872,856 A | 3/1975 | Clayton | |
| 4,554,909 A | 11/1985 | Pino y Torres | |
| 5,653,683 A | 8/1997 | D'Andrea | |
| 5,720,717 A | 2/1998 | D'Andrea | |
| 5,947,891 A | 9/1999 | Morrison | |
| 6,390,968 B1 | 5/2002 | Harmon | |
| 2002/0055666 A1 | 5/2002 | Hunter et al. | |
| 2003/0153803 A1 | 8/2003 | Harmon | |
| 2005/0049509 A1 | 3/2005 | Mansour et al. | |
| 2005/0220882 A1 | 10/2005 | Pritchard et al. | |
| 2006/0014997 A1 | 1/2006 | Kindlein et al. | |
| 2006/0173235 A1 | 8/2006 | Lim et al. | |

*Primary Examiner*—Charles A Marmor, II  
*Assistant Examiner*—Christine D Hopkins  
(74) *Attorney, Agent, or Firm*—Thomas M. Freiburger

(57) ABSTRACT

A customized gynecological brachytherapy applicator is formed by placing a molded balloon, which is secured to a handle, into a vaginal cavity and then filling the mold balloon with a settable liquid material. The material may be an expanding foam or any other form of curable material that becomes solid, rigid or pliable, when set by chemical action, temperature change, oxidation, a curing means such as a light, or other curing regime. The mold balloon can be elastic or inelastic, depending on the degree to which the applicator is to conform its external surfaces to the vaginal contours. One or more lumina are provided in the set filler material to receive a radiation source, with additional lumina optionally provided for purposes such as drainage or administration of therapeutic agents. The applicator may be withdrawn and reinserted into the vagina during treatment, and selected tissues adjacent to the applicator are irradiated in accordance with a radiation prescription.

10 Claims, 8 Drawing Sheets

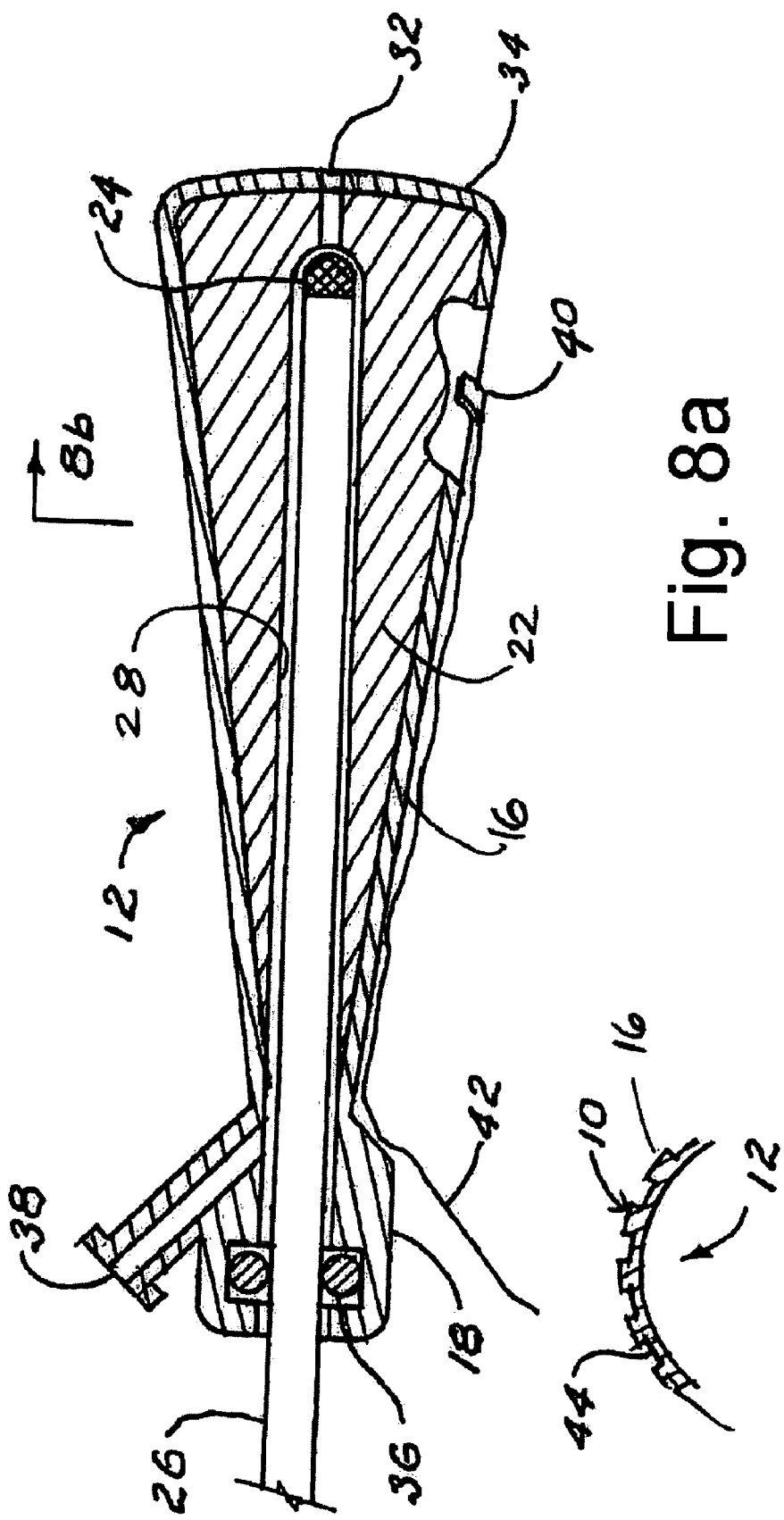

CUSTOMIZED GYNECOLOGICAL BRACHYTHERAPY APPLICATOR AND METHOD

BACKGROUND OF THE INVENTION

This invention concerns radiation therapy, especially brachytherapy, for treating tissues which may have diffuse proliferative disease. In brachytherapy, the radiation source is generally placed within a surgically created or naturally occurring cavity in the body. In particular, this invention relates to an applicator for delivering radiation therapy to a vaginal cavity and/or to adjacent tissue, often following surgical treatment of cancer. Radiation therapy of this sort is generally administered over a period of time in partial doses, or fractions, the sum of which comprises a total prescribed dose. This fractional application takes advantage of cell recovery differences between normal and cancerous tissue whereby normal tissue tends to recover between fractions, while cancerous tissue tends not to recover.

In brachytherapy, a prescribed dose is selected by the therapist to be administered to a volume of tissue (the target tissue) lying outside the treatment cavity into which the radiation source will be placed. Generally the prescribed dose will include a minimum dose to be delivered at a preferred depth outside the treatment cavity (the prescription depth). Since, in accordance with the laws of physics, radiation intensity falls off with increasing distance from the radiation source, it is desirable to create and maintain a space between the source of radiation and the first tissue surface to be treated (generally the cavity wall since the source is placed within the cavity) in order to moderate the absorbed dose at the cavity surface. Although not always the case, generally the absorbed dose at the prescription depth outside the cavity is to be uniform. In this isotropic case, it is therefore important that the incident radiation on the interior surface of the cavity be the same at all points being treated. To accomplish this objective, it may be necessary to sequentially position a single radiation source through a series of positions (or utilize multiple sources strategically placed) which, in the aggregate, produce a uniform absorbed dose incident on the cavity surface being treated. When this is achieved, the absorbed dose reaching into tissue will be the same at all points being treated, and the minimum prescribed dose can be delivered at the prescription depth as nearly as the treatment plan will allow. Furthermore, by selecting the radiation source intensity (radioisotope emissions or X ray tube output) and controlling treatment time and the distance from the source(s) to the cavity interior surface, the incident radiation can be sufficiently moderated to avoid substantial damage to normal tissue.

Rigid applicator cylinders designed to receive radioisotopes have traditionally been used to treat vaginal cancer or malignancies in adjacent tissues. A principal function of an applicator is to establish and maintain distance relationships between the radiation source and the tissues being treated such that the prescribed dose is delivered to a desired prescribed depth of tissue, and yet normal tissues nearest the radiation source are not subjected to absorbed doses sufficient to risk significant necrosis. Applicators of this general type are available, for example, from Varian Medical Systems, Inc., Charlottesville, Va. Such prior art applicator cylinders are sized to the vaginal cavity or adjacent anatomy, but because the tissues should be positioned closely against the exterior surface of the applicator, large applicators must be chosen that are often painful on insertion, and once inserted still fail to provide a good fit. Additionally, prior art cylinders are generally straight, with a central lumen into which radioactive seeds are delivered and later removed after completion of prescribed therapy. As a result, anisotropic treatment plans are difficult to achieve with such symmetrical applicators. Thus conventional applicators are less than ideal in many cases.

SUMMARY OF THE INVENTION

Although this invention is disclosed with specific reference to therapeutic application of radiation within the vagina, the principles of this invention may be similarly applied to other brachytherapy situations in other natural or surgically created anatomic spaces, or to therapeutic situations other than postsurgical treatment of cancer, and still fall within the bounds of this invention.

This invention provides a personalized or customized applicator specific to the individual patient for whom radiotherapy is intended. By this invention, a core portion of the applicator is fashioned within the individual patient's vagina. A semi-rigid or expandable form or mold is positioned within the vagina serving as a form balloon, and is filled with an amount of material sufficient to fill the vagina to a desired degree and thereby to facilitate delivery of a prescribed radiation dose to adjacent or surrounding tissues. Silicone rubber is one preferable mold material and suitable molds can be fabricated by dip-and-cure or molding processes well known to those skilled in the art.

The filler material is preferably capable of undergoing a reaction in which, as examples, a change of state occurs, a foaming process takes place or in which a sufficient change in viscosity occurs such that the cast or molded-in-place applicator retains shape integrity sufficient to allow repeated removal and insertion. Such materials would include reactive gels or polymers, with or without foaming agents, and thermoset materials, all with radiation attenuation and tolerance characteristics within practical limits allowing for delivery of radiation to the target tissues. Within tissue-tolerance limits, thermoset and exothermal filler material reactions can be used, or artificial heating applied, for example from within channels within the mass of filler material being formed, to provide the applicator with sufficient form stability in the desired shape. Furthermore, if adjustment of the general molded-in-place configuration is desired to facilitate isodose manipulation or tissue positioning different from the as-molded shape, thermoplastic materials can be used, such that after removal of the as-molded applicator from the vagina, heat can be used to soften the material, allowing reforming and subsequent cooling in a more desirable configuration. If used, thermoset material can be deliberately cured only partially within the vaginal cavity, and if necessary, further cured to completion of the reaction outside the vagina, and perhaps after any desired shape adjustment.

The mold itself can be polymeric and act like a condom responding to internal pressure applied by the pressure of filling, by a fill reaction taking place within the (preferably closed) confines of the mold, or by a combination thereof. If filling is by a reaction within a closed space, the dynamics as well as the temperature and pressure limits of the reaction must be well understood. Pressure relief may be provided if necessary, for example, by conventional valving. Alternately, the mold may be inelastic and resist expansion, thereby tending to shape the cavity to the predetermined and desired shape of the mold. Such a mold is flexible (bendable) but substantially inelastic, as in the properties of a Mylar balloon versus a latex balloon.

A channel or channels to position the radiation source or other instrumentation within the applicator can be molded in place within the vagina during the filling (and harden or cure) process by positioning coring within the mold such that the filler material forms around the cores simultaneously with filling of the mold. The coring can be stripped from the filled applicator either from within the vaginal cavity, or after removal. Using this alternative, the coring need not be straight, permitting channels of any configuration consistent with the filling or molding process, and also consistent with the prescribed therapy. Alternatively, the channels can be drilled or otherwise fashioned outside of the vagina as desired after the filling process. In addition to channels created for introduction of radiation sources into the applicator, channels to permit suction, drainage, or infusion of liquid or gaseous agents may be provided by similar form-in-place techniques, and configured to communicate with the outer surface of the applicator in desired locations. Some embodiments may include texturing or channeling of the outer applicator surface in order to facilitate fluid flow between the surface of the applicator and the anatomic or treatment cavity.

The portion of the applicator outside the body is connected to the mold balloon, and may optimally comprise a handle which extends outside the vaginal cavity to facilitate insertion and removal of the applicator, or with other manipulation as may be desirable. Such an applicator used by and holding a prefabricated handle external of the anatomy during the molding process such that essentially an extension of the handle is cast or molded to the applicator forming a monolithic structure manipulable via the handle. Conversely, the mold which contains the filler material may be sufficiently long that it extends outside of the body and once filled, serves as a form of handle for manipulation.

After such an applicator is fashioned to mimic the interior surface of the vaginal cavity, and after any secondary shaping and coring is complete, the applicator is ready for use. Following a prescription prepared by competent personnel, dose planning may proceed such that, based on the applicator shape and the radiation delivery parameters of the specified radiation source, the source positioning and exposure times are determined, with the aggregate exposure conforming as closely as possible to the prescription. After patient preparation, the applicator is inserted into the vaginal cavity and positioned in a manner consistent with delivery of the therapy to the prescribed plan. The radiation sources can then be introduced into the applicator and manipulated according to the plan. In the case of an isotope source, this may involve therapy being carried out within a bunker with use of an afterloader to comply with safety requirements. With an electronic x-ray source, for example that of the Axxent® system by Xoft, Inc. (Fremont, Calif.), the radiation source can be handled casually and therapy can be administered with comparatively less shielding.

If desired and once the isodose characteristics of the source are understood, the applicator may be fitted with a radiation sensor or sensors, for example, of the MOSFET type, in a manner which does not interfere with administration of the prescribed treatment, and sensor feedback can be used to monitor, correct and/or verify proper dose delivery. Correction based on feedback can be applied, for example by manual or automated adjustment during or between fractions, in real time in the sense that the adjustments are made as the procedure progresses. Communication from the sensor(s) can be by conventional hard wiring or may be wireless.

DESCRIPTION OF THE DRAWINGS

In the following figures, cancerous regions of anatomy are shown shaded. These figures, together with the written description herein, describe the present invention.

FIG. 8a depicts, in section view, an applicator in which the coring passes through the full length of the applicator so as to communicate with the interior of the vaginal cavity. A source and catheter are shown positioned within the applicator.

FIG. 8b depicts a small section of the wall of the applicator mold showing grooves in the outer surface of the wall.

DESCRIPTION OF PREFERRED EMBODIMENTS

Applicators of this invention are formed in situ within the patient's vagina, preferably by insertion of a mold into the vaginal cavity, into which a filler material may be introduced so as to expand the mold, thus filling the vagina. After introduction, the filler may undergo a physical or chemical reaction to create a substantially rigid member customized to and in conformance with the patient's vaginal cavity, or to facilitate delivery of a radiotherapy prescription. Such a technique seeks to eliminate any air spaces between the applicator and vaginal cavity since it is known that such spaces detract from optimal application of radiation therapy. Filling of a mold in situ is preferable to filling the vagina directly with a filler material in that most fillers are of a form that is introduced at a relatively high temperature and cooled to set their shape, or they undergo a chemical reaction by which they are cured in the desired shape. With proper design, use of a mold can serve to insulate the tissues from undesirable thermal or chemical exposure. Thermal or chemical fillers, directly applied within the vagina, can cause discomfort to the patient, if not outright injury.

Figure 1:
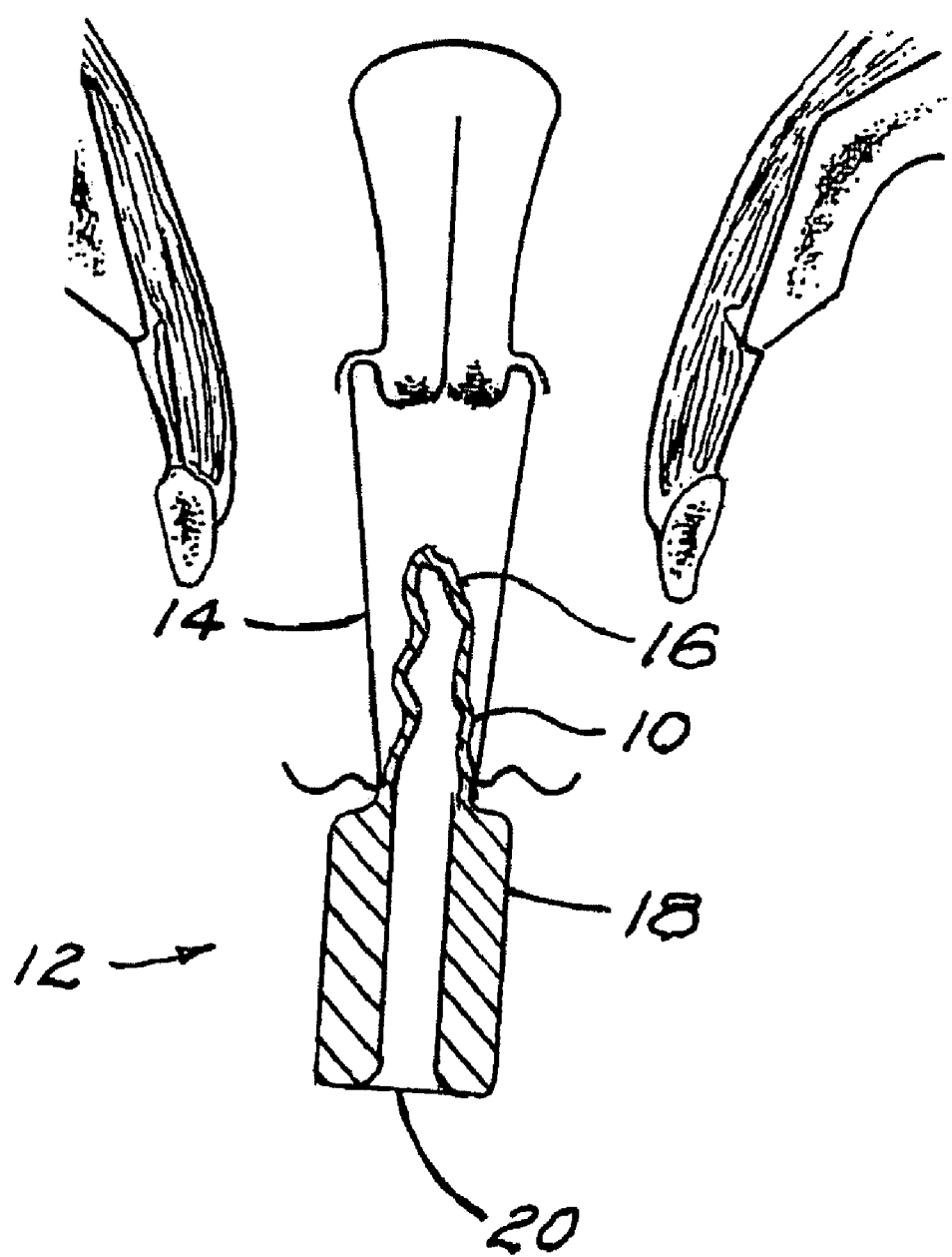
FIG. 1 depicts an applicator mold in coronal section through the vaginal space prior to filling the mold with filler material.

FIG. 1 shows a mold 10 of an applicator 12 of the invention positioned in an uninflated condition within the vagina 14 of the patient. The mold comprises a hollow distal portion 16, i.e. a mold balloon, capable of being distended in response to application of internal pressure so as to fill the vaginal cavity of the patient. In one preferred embodiment, the mold balloon 16 distends so as to elastically conform generally to the shape of the vaginal cavity, expanding the soft-tissue cavity to a desired degree. In an alternate embodiment, the mold distal portion 16 preferably is flexible but substantially inelastic and, upon application of internal pressure, will expand to a preferred configuration, filling (expanding) and shaping the vaginal cavity, but at the same time bending or curving to follow the anatomy, and in this sense generally conforming to the vaginal anatomy. The applicator 12 preferably further comprises a relatively rigid and tubular proximal portion serving as a handle 18 for the therapist, facilitating manipulation of the applicator 12 within the vagina 14, including its removal and insertion in the course of treatment. The lumen 20 of the handle 18 communicates with the hollow interior of distal portion or mold balloon 16.

The material of the mold balloon 16 is preferably thin and polymeric, silicone rubber being an example material for an elastic embodiment, and PET (polyethylene terephthalate) being an example for an inelastic embodiment. The material of the mold balloon 16 can be loaded with a radio-opaque material, for example barium sulfate or bismuth subcarbonate, to facilitate imaging the applicator in the patient's body by conventional radiographic means, and for treatment planning purposes. The balloon material is lightly doped with radio-opaque additive so as to reveal a "shadow" with external imaging but not so heavily so as to significantly attenuate radiation directed outwardly by a source in the applicator. The material of the proximal handle 18 may be the same material as the distal portion (e.g., integrally formed), but of different geometry so as to provide greater rigidity to the handle portion. Alternatively, the proximal handle 18 may be of a different material, for example polycarbonate to which the distal, distendable portion 16 may be bonded or mechanically fastened using conventional methods. The mold portion 16 and handle 18 may be made by conventional dipping or molding processes, and if not monolithic, may be joined by conventional secondary fastening methods. Such molding, bonding and fastening processes are well known to those skilled in the medical device arts.

Figure 2:
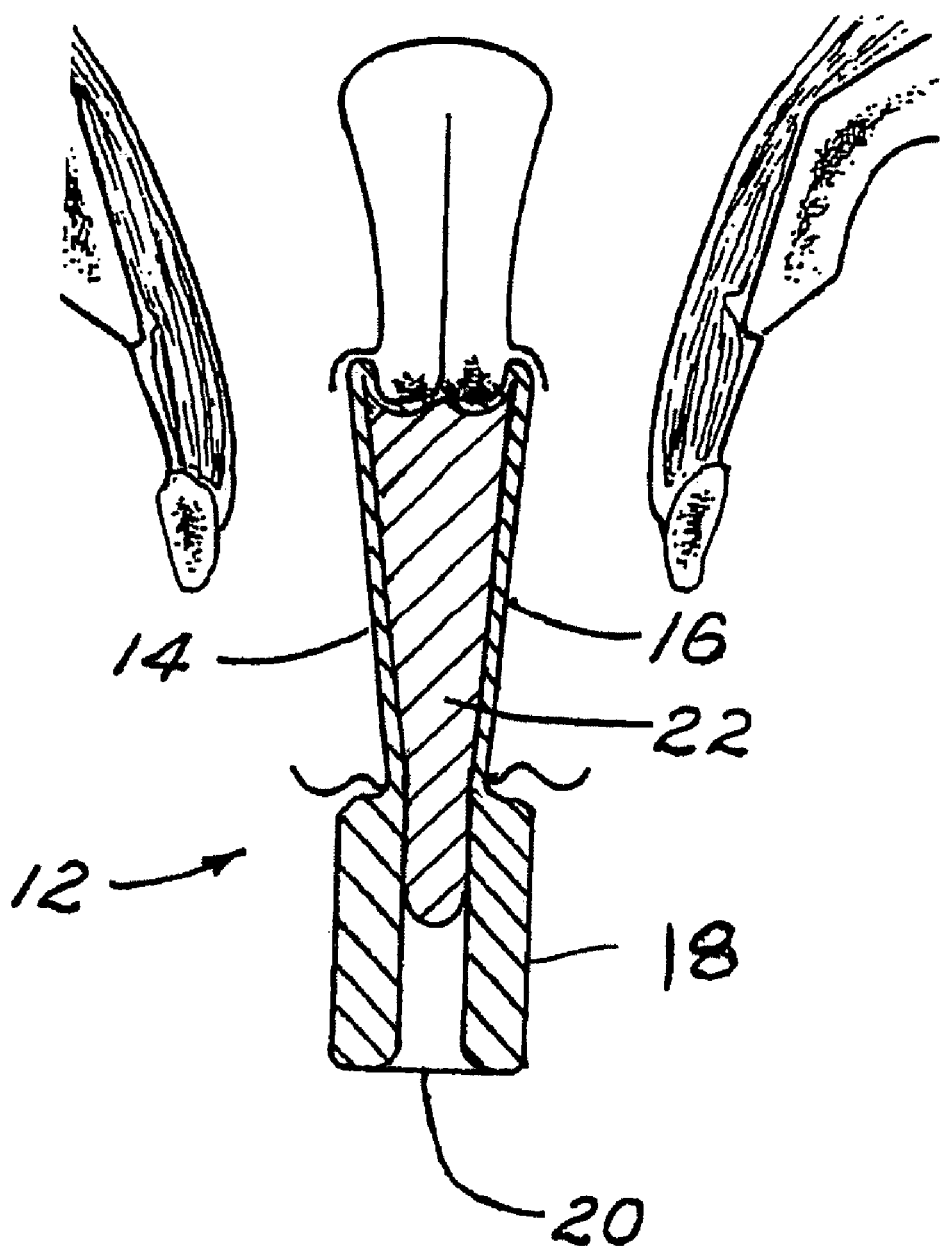
FIG. 2 depicts the mold of FIG. 1 in coronal section after filler material has been placed within the mold and the mold expanded to occupy and conform to the vaginal cavity.

FIG. 2 shows the mold 10 positioned within vagina 14. The filler 22 has filled the mold of FIG. 2, distending the distal portion of the mold 16 until the mold 10 completely occupies and optionally expands the cavity of the vagina 14. The filler 22 preferably extends at least partially into the handle 18 providing further structural rigidity to the handle. The filler 22 can comprise a settable reactive liquid which can be injected into the mold 10 through the handle lumen 20. Sufficient filler can be injected into the mold 10 under controlled pressure to forcibly distend the mold distal portion 16 until it expands the vaginal cavity to the desired degree. Confirmation of complete filling can be visualized by x-ray or other convention imaging technique. The liquid filler, which may be initially two or more parts that are mixed, for example at injection, will react to form a relatively stable, solid form by any of several conventional methods. For example, a chemical reaction can be initiated, either by waiting an appropriate time, for example by use of polyurea component materials and/or by curing. Alternatively, a catalyst reaction can be initiated, for example by mixing the catalyst (for example, platinum in silicone) during injection and subjecting the injected material to ultraviolet light or to another initiator to start a curing reaction. Other liquid-to-solid chemical reactions known to those of skill in the art may also be used. Alternate chemistry involving foaming materials can also be used. Spontaneous reactions like that described above can be used, as can other reactions requiring an initiator can be used, such as moisture cured polyurethanes. The liquid injected into the mold can cure or set to a soft rubbery consistency, such as a silicone material, or it can be an expanding foam that becomes semi-rigid but somewhat flexible (generally rigid), or it could be another liquid which is injected and does not expand to any appreciable degree but simply is cured to a rigid or semirigid consistency by any of the techniques mentioned above or other known techniques. Note that if the mold balloon is inelastic, the point of complete filling will be easily determined by the pressure rise at injection. If the balloon is elastic, however, the filling can be done by injecting a predetermined volume or injecting the liquid up to a predetermined pressure, or simply injecting liquid until external imaging determines the desired fill has been reached. One class of potential filler materials exhibiting desirable properties suitable for applicator filler material is dental impression material.

Physical reactions can also be used to create a solid applicator form. A material having relatively abrupt melting and freezing points with little hysteresis, which is viscous when warmed to temperatures slightly above body temperatures, can be injected into the mold 10, and allowed to cool in situ, forming a rigid applicator 12. An example of such a material would be a low-melting paraffin wax. A form produced in this manner can also be used as a pattern to generate a secondary shape by conventional molding or casting techniques. This secondary shape can then be used as the actual applicator during treatment.

Figure 3:
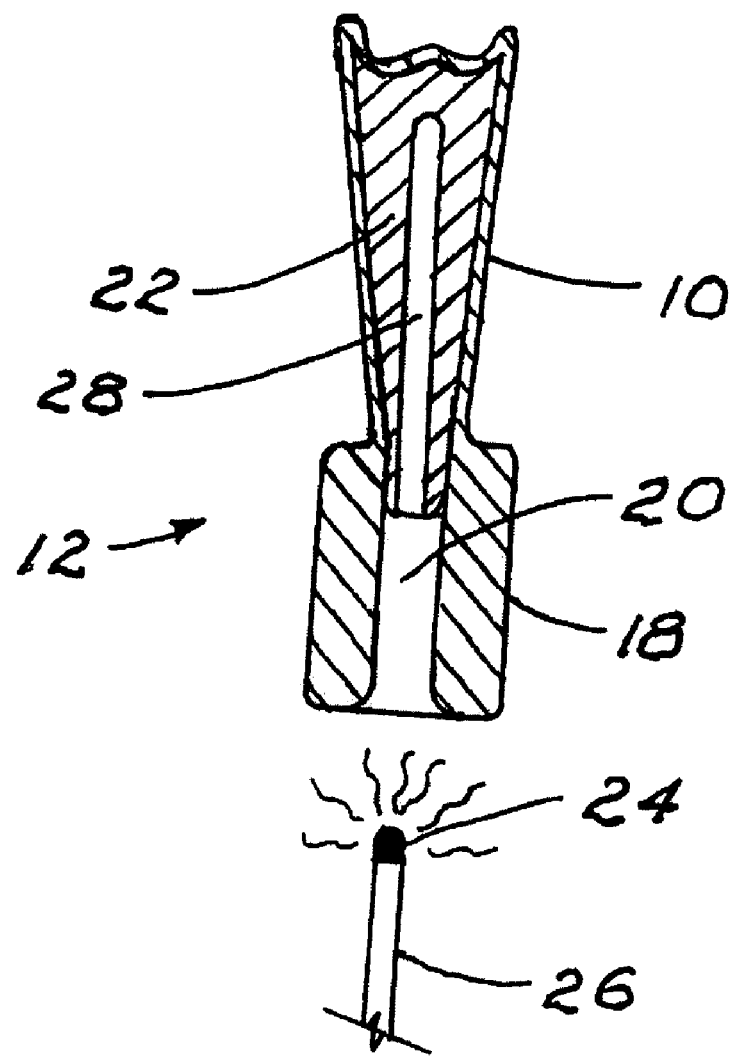
FIG. 3 depicts in cross section, the filled applicator of FIG. 2 withdrawn from the vagina and after having been cored to accept a radiation source positioned at the end of the catheter. A radiation source at the end of a catheter is shown adjacent the entry to the cored hole in the applicator, said catheter and source being configured to emit radiation in a substantially radial and distal direction.

FIG. 3 shows a mold filled with a filler material as described above in connection with FIG. 2, having been allowed to assume its relatively rigid shape mimicking the vaginal cavity and then having been removed. The filler 22 is shown having been cored to form an interior lumen 28 within the filler 22. As shown, lumen 28 connects with the handle lumen 20 and extends from within handle 18 distally, but not completely through the filler 22. The purpose of this lumen is to accommodate the radiation source 24 and source catheter 26 for purposes of irradiating the interior of the vaginal cavity. Formation of the interior lumen 28 may be done in situ within the vagina by use of a lumen-forming obturator or core (not shown) held in proper position during the filler material injection and forming process. Alternatively, the cored lumen 28 may be formed by a secondary drilling or similar operation after the filling process (without an obturator positioned in place) has been completed, and after the filled mold 10 has been withdrawn from the vagina 14.

If desired, the location of the lumen 28 may be selected to achieve radiation dose profiles which address the specific morbidity of the particular patient for whom the applicator 12 is intended. Alternately, if placed centrally within the filled shape of the applicator, the positioning of the radiation source 24 within the lumen 28 can be programmed to create a uniform dose at the exterior of the applicator 12 and at the surface of the vaginal cavity. Thus, a uniform prescribed dose at the prescription surface (the imaginary locus of all points at the prescription depth, hence an isodose surface) can be achieved. Different positioning of the lumen 28 and the source 24 can be used to create other radiation dose profiles as desired.

As noted above, FIG. 3 also shows a radiation source 24 mounted at the tip of a source catheter 26. In this case, the catheter preferably includes a shield (not shown) assuring that the radiation is emitted from the source radially and distally only, not proximally. Without such shielding, the source 24 could be fashioned to emit substantially isotropically, or with different shielding configurations, in other desirable patterns. Shielding is more fully explained in copending U.S. patent application Ser. No. 11/471,277, and preferred radiation sources (miniature x-ray sources) are disclosed in U.S. Pat. No. 6,319,188. These disclosures are incorporated by reference herein in their entirety. Other sources may be used as well, including isotope sources, for example as available from Varian Medical Systems, Inc., Charlottesville, Va.

Figure 4:
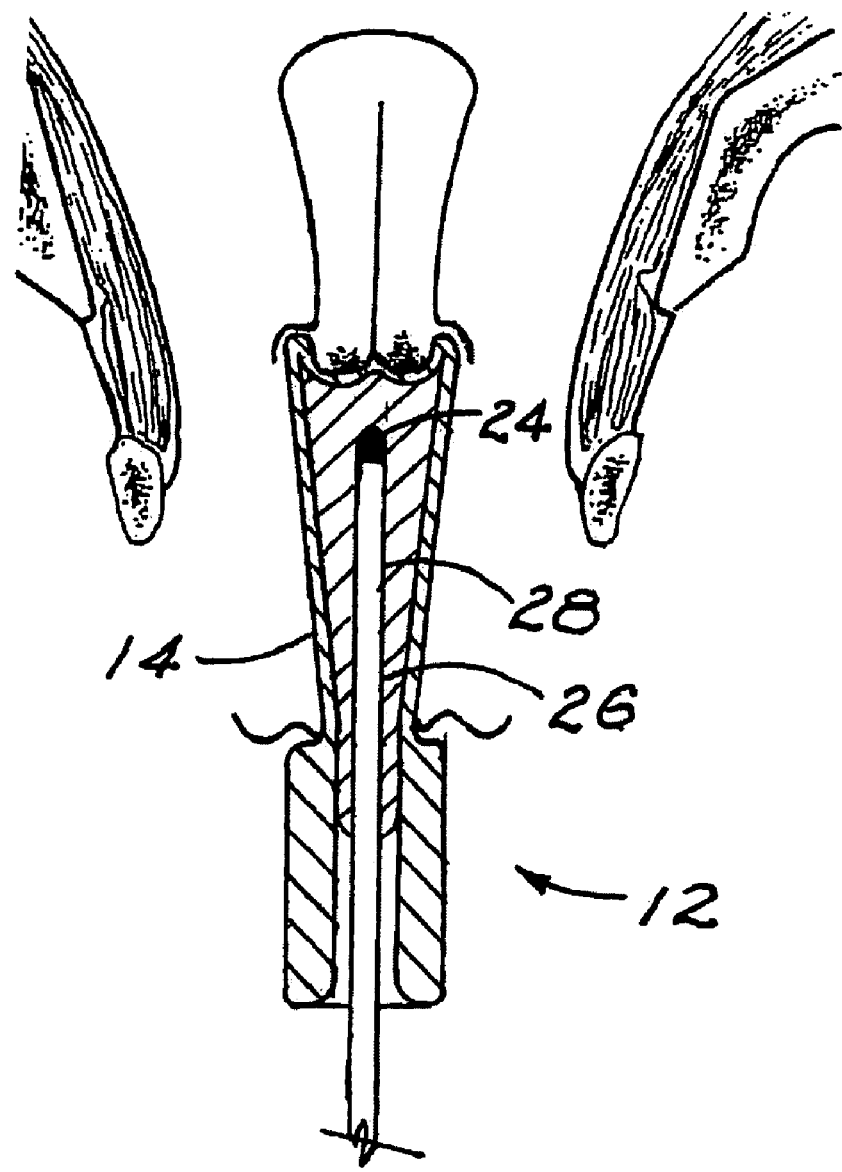
FIG. 4 depicts in coronal section, the applicator, source and catheter positioned within the vaginal space to irradiate the tip of the cervix.

FIG. 4 shows a completed (filled and cored) applicator 12 after insertion into the vagina 14. A source catheter 26 and source 24 are in position within the applicator lumen 28 to commence radiation treatment. As in FIG. 3, the source and catheter preferably are configured and/or shielded to direct the radiation distally and radially in order to treat cancer at the tip of the cervix, as indicated. If desired, a single source may be positioned sequentially through different positions and dwell times within the applicator lumen to create, in the aggregate, a prescribed absorbed dose pattern. Alternatively, the applicator may comprise multiple lumina for source positioning, either at the outer region of the filler at or near the mold balloon surface or more deeply within the body of the applicator. Single or multiple sources may be utilized to create the desired absorbed dose pattern. For clarity, multiple lumina within the applicator structure are not shown, but their incorporation by those of skill in the art will be readily apparent.

Figure 5:
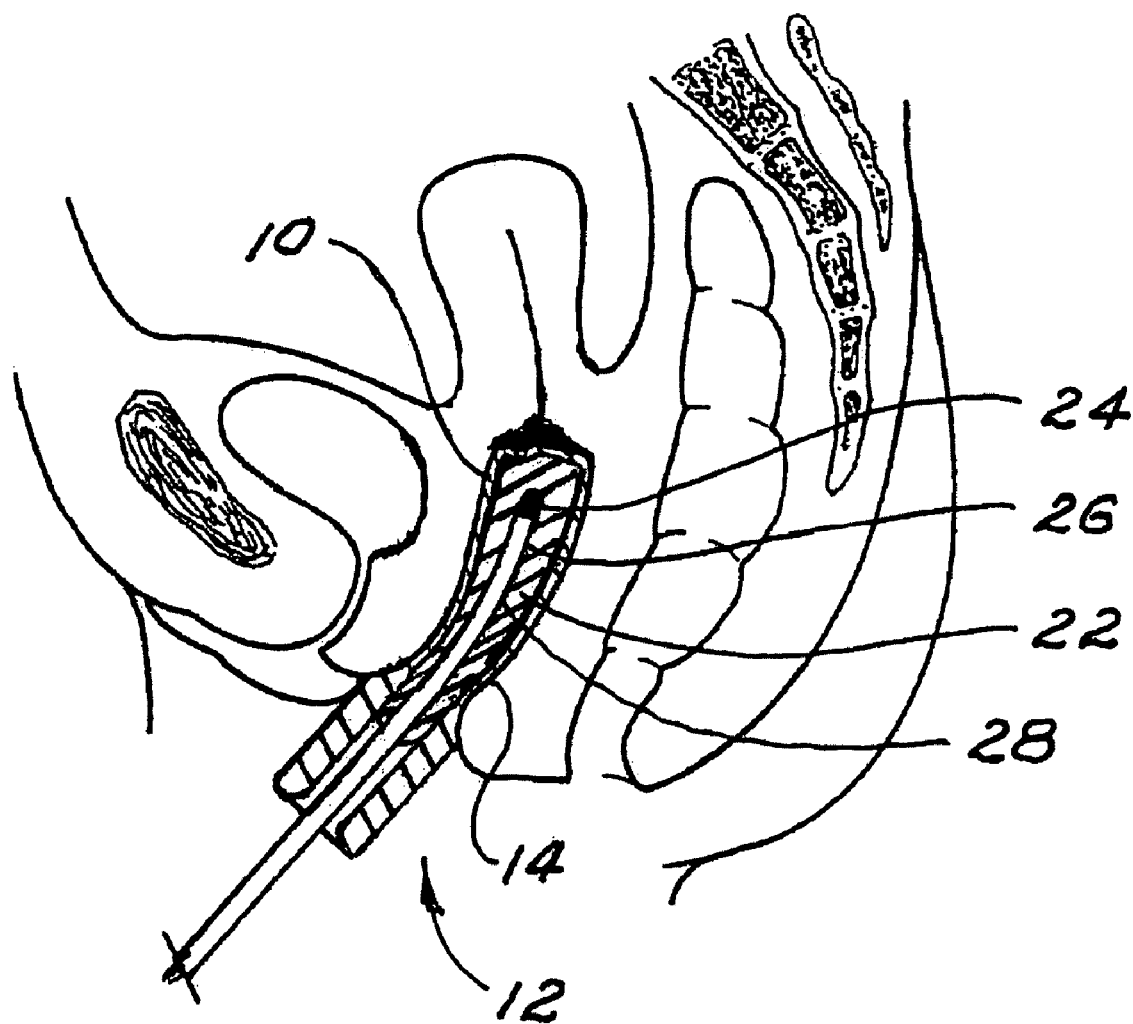
FIG. 5 depicts the apparatus of FIG. 4 in sagittal section, positioned within the vaginal space to irradiate the tip of the cervix.
Figure 6A:
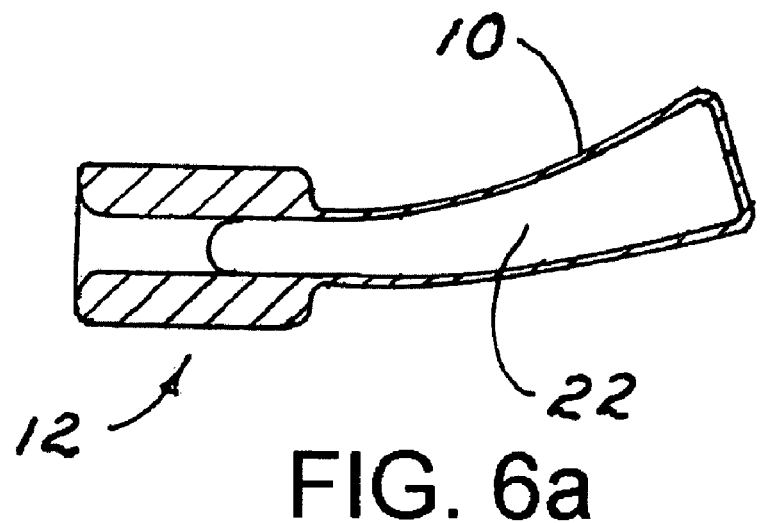
FIG. 6a depicts the applicator of FIG. 2 in section view corresponding to the sagittal section of FIG. 5, the applicator having been removed from the vaginal space after filling.
Figure 6B:
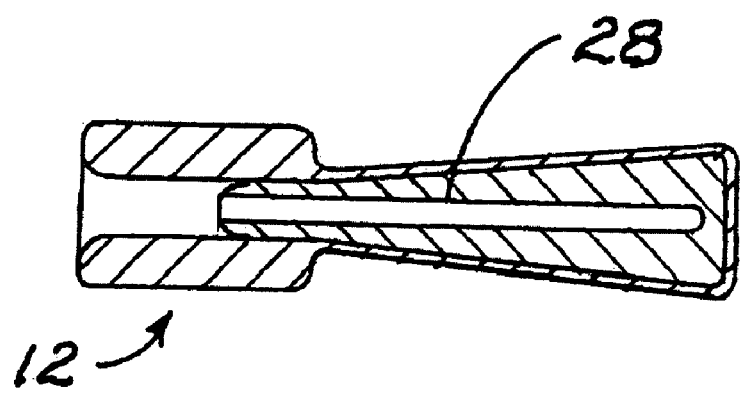
FIG. 6b depicts the applicator of FIG. 6a in section, the applicator having been straightened to facilitate coring. Coring is shown in a manner in which the distal end of the core hole stops short of the distal extremity of the applicator.
Figure 6C:
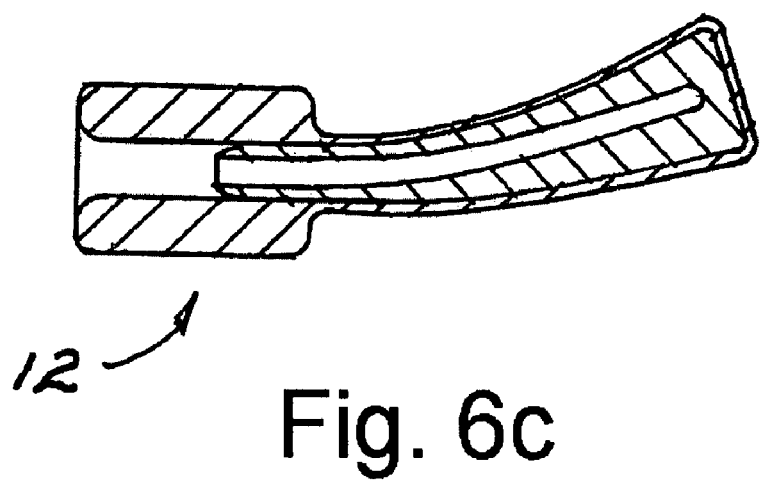
FIG. 6c depicts the applicator of FIGS. 6a and b after coring, having been recurved to the shape of FIG. 6a to facilitate a proper fit within the vagina when reinserted.

FIG. 5 shows a sagittal view of the applicator 12, source 24 and catheter 26 of FIG. 4. Again, the radiation preferably is directed radially and distally as in FIG. 4. Note that the applicator is cored with the lumen 28, and the axis of the applicator 12 is curved, conforming to the patient's anatomy. If the applicator is filled without forming the lumen in situ, a preferred method of providing such a cored lumen having a curved shape is to use a filler 22 which may be formed as described previously, and which is resilient or semi-rigid, or capable of being temporarily reformed after extraction of the applicator 12 from the vagina 14, for example by application of mechanical force. Such reforming might be aided by application of heat as would be the case for a thermoplastic filler material. By such methods, the extracted applicator can be straightened for drilling or other coring operations to create the lumen 28 for the source 24 and the catheter 26. Once cored, the applicator 12 can be again reformed to its original curved shape, again inserted into the vagina 14, and radiation treatment commenced. Such a sequence of coring steps is shown in FIGS. 6a through 6c. FIG. 6a shows the applicator 12 as removed from the vagina after the filler 22 has been placed in the mold 10. FIG. 6b shows the applicator 12 straightened and cored, with the lumen 28 so formed extending almost through the entire length of the applicator 12. FIG. 6c shows the applicator 12 once again in a curved configuration, ready for reinsertion into the vagina.

Figure 7:
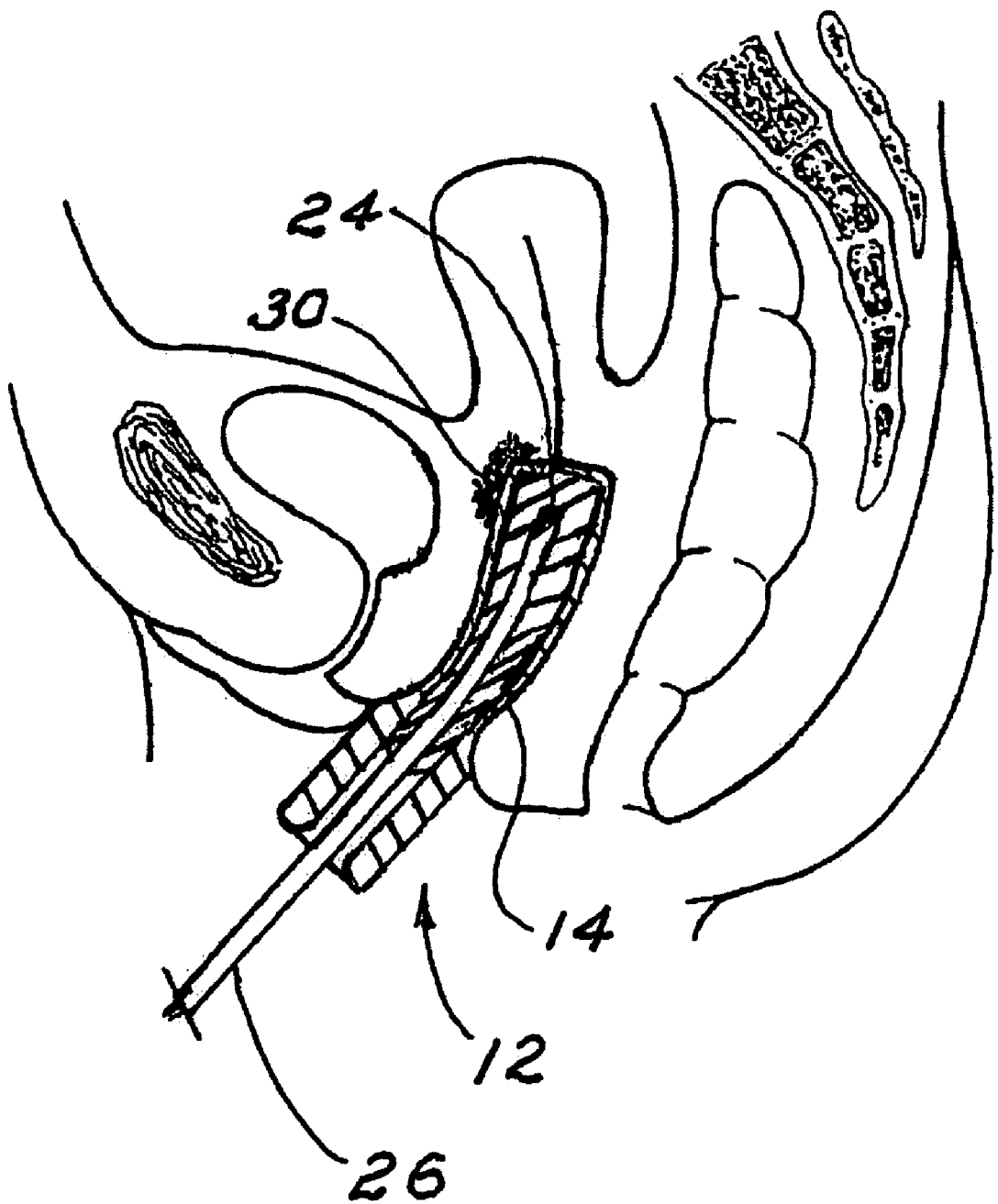
FIG. 7 depicts in medial sagittal section, the applicator of FIG. 6c reinserted into the vaginal space, with a source and catheter positioned within the cored hole of the applicator. The source and catheter are configured to emit radiation laterally in order to irradiate a lesion on the anterior wall of the vagina.

FIG. 7 again shows an applicator 12 of the invention inserted in the vagina 14 of a patient similar to that shown in FIG. 5, but this patient presents with a lesion 30 of the anterior formix of the vagina. In FIG. 7, the source 24 and catheter 26 are configured with shielding to direct radiation generally in a radial direction, and the angular orientation is controlled such that the radiation treatment is brought to bear on the lesion in the anterior direction. Again, methods for radiation shielding in the manner described can be found in copending application Ser. No. 11/471,277, referenced and incorporated herein above.

FIG. 8a shows an alternate applicator embodiment 12 with the mold balloon 16 filled and the filler 22 cored generally according to the methods described above. In this embodiment, however, the cored lumen 28 in the filler 22 communicates through a port 32 with the outer surface 34 of the applicator 12 such that fluid may pass through the catheter lumen outside of the catheter 26 and into or out of the vaginal space. In FIG. 8a, the port 32 opening into the vaginal space is shown as an axial extension of the catheter lumen 28. Alternatively, a port or ports 32 may connect the catheter lumen 28 and outer applicator surface 34 at any position or positions desired, to suit any purpose, as examples, for venting or draining the vaginal space outside the applicator, or for administering liquid agents to the inner surface of the vagina during or in connection with treatment. The handle portion 18 of the applicator 12 of this embodiment includes a conventional seal 36, for example an "0" ring seal, to prevent fluid leakage between the catheter 26 and the handle 18. The handle of this embodiment also comprises hub features including a fluid access port 38 leading to the catheter lumen 28 to complete the communication path from outside the body to the vaginal space when the applicator is positioned within the vagina.

FIG. 8a also shows a radiation sensor 40 affixed to the outer surface 34 of the mold balloon 16 (it could be on the inner surface). If the source 24 is characterized in a manner confirming stable operation and which relates its output at the position of the sensor 40 for each treatment position during therapy, the output of the sensor 40 may be used to verify treatment to plan, and/or to provide feedback for real-time control of the radiation delivered. Real time is intended to mean that radiation is adjusted in some way as the procedure continues, or prior to its conclusion, in response to measurement of radiation received at the sensor. Such sensor output can be communicated through a connecting wire 42 between the sensor 40 and a controller (not shown) which adjusts radiation source position, or in the case of an electronic x-ray source, can also control source output. Communication between the sensor and the controller can alternatively be by wireless methods. If desired, multiple sensors can be employed, and positioned on the surface of the applicator at the vaginal wall, or within or between elements of the applicator. Such an array of sensors can be interrogated sequentially during treatment, or monitored continuously.

FIG. 8b shows in partial section, a portion of the mold 10 of the applicator 12, specifically of the mold balloon 16. On the outer surface 34 of the mold balloon 16 is a pattern of grooves 44. These grooves may cover all or only a portion of the outer surface 34 of the mold balloon, and provide for liquid movement at the interface between the vaginal cavity surface and the applicator 12. Acting together with the port or ports 32, fluids may be administered or withdrawn from the applicator/ vagina interface. Furthermore, if the pattern of grooves 44 extends proximally of the vaginal opening onto the handle surface, the grooves can function to vent any fluid trapped between in the applicator/vagina interface without need for ports 32.

This invention has been described herein in considerable detail in order to instruct one of skill in the art how to practice the invention. It is to be understood, however, that the invention can also be carried out by other methods and apparatus without departing from the scope of the invention itself.

We claim:

1. A method for application for brachytherapy treatment to vaginal tissue, comprising:
   providing a handle with an axial opening therethrough, configured to be positioned outside the mouth of a vagina, with a flexible, conformable, inflatable mold balloon connected to a distal end of the handle as an extension of the handle, the mold balloon having a closed distal end and being sufficiently flexible to conform to vaginal interior tissue surfaces when inflated,
   using the handle, inserting the mold balloon into a vagina,
   admitting a conforming, essentially liquid, settable filler material into the mold balloon via the opening through the handle, with the balloon in the vagina, causing the mold balloon to expand and conform to the vaginal interior tissue surfaces, and curing the filler material in situ to form a custom-fitted gynecological brachytherapy applicator,
   providing a generally axially-extending lumen in the filler material, and
   with the custom-fitted applicator in the vagina, and with a radiation source in the lumen of the applicator, commencing irradiation of tissue adjacent to the applicator.

2. The method of claim 1, wherein the lumen is provided by coring the lumen into the filler material.

3. The method of claim 1, wherein the filler material is an expanded foam.

4. The method of claim 1, wherein the filler material is a thermosetting material.

5. The method of claim 1, wherein the radiation source is a controllable electronic x-ray tube.

6. The method of claim 1, further including a radiation sensor positioned in the applicator, and including monitoring radiation received at the sensor during the radiation procedure, with a monitor connected to receive dose measurement signals from the sensor.

7. The method of claim 6, wherein the radiation sensor is on the mold balloon so as to be adjacent to tissue is in use of the applicator.

8. The method of claim 6, wherein the radiation source is an electronic controllable x-ray source, and the method further including, using the monitor and an associated controller modifying the radiation emitted from the x-ray source in real time as the procedure continues, in response to dose information received by the controller.

9. The method of claim 1, including, following curing of the filler material, coring a distal port through the distal end of the applicator to provide a path for fluid withdrawal from or for delivery of therapeutic liquids to the vaginal cavity.

10. The method of claim 9, wherein the handle has a hub at its proximal end, the hub providing a fluid access port communicating with the cored lumen and the distal port.

* * * * *